US008663284B2

(12) United States Patent  (10) Patent No.: US 8,663,284 B2
Beger et al.  (45) Date of Patent: Mar. 4, 2014

(54) SPINAL COLUMN STABILIZATION SYSTEM, CONNECTING ELEMENT FOR A SPINAL COLUMN STABILIZATION SYSTEM AND METHOD OF MANUFACTURING SUCH A CONNECTING ELEMENT

(75) Inventors: Jens Beger, Tuttlingen (DE); Fabian Hoefer, Tuttlingen (DE); Berthold Hohl, Tuttlingen (DE); Stefan Schmid, Mühlheim (DE); Josef Heine, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 188 days.

(21) Appl. No.: 13/231,496

(22) Filed: Sep. 13, 2011

(65) Prior Publication Data
US 2012/0071927 A1  Mar. 22, 2012

(30) Foreign Application Priority Data

Sep. 20, 2010 (DE) .......................... 10 2010 037 665
Oct. 21, 2010 (DE) .......................... 10 2010 060 112

(51) Int. Cl.
*A61B 17/70* (2006.01)
(52) U.S. Cl.
USPC ............................ 606/255; 606/254; 606/257
(58) Field of Classification Search
USPC .................................................. 606/250–279
See application file for complete search history.

(56) References Cited

U.S. PATENT DOCUMENTS

| 7,335,200 | B2 | 2/2008 | Carli |
| 7,815,663 | B2 | 10/2010 | Trieu |
| 7,833,256 | B2 | 11/2010 | Biedermann |
| 2005/0203511 | A1* | 9/2005 | Wilson-MacDonald et al. ................. 606/61 |
| 2006/0064090 | A1* | 3/2006 | Park ................................ 606/61 |
| 2006/0184171 | A1 | 8/2006 | Biedermann |
| 2006/0229608 | A1* | 10/2006 | Foster et al. .................... 606/61 |
| 2007/0191832 | A1 | 8/2007 | Trieu |
| 2008/0234736 | A1 | 9/2008 | Trieu |
| 2010/0042154 | A1* | 2/2010 | Biedermann et al. ......... 606/254 |
| 2010/0069964 | A1 | 3/2010 | Lechmann |
| 2010/0211106 | A1* | 8/2010 | Bowden et al. ............... 606/260 |
| 2011/0054534 | A1 | 3/2011 | Biedermann |
| 2011/0245875 | A1* | 10/2011 | Karim .......................... 606/263 |
| 2013/0035725 | A1* | 2/2013 | Beger et al. ................... 606/278 |

FOREIGN PATENT DOCUMENTS

| DE | 10004712 C1 | 8/2001 |
| DE | 102004018621 A1 | 11/2005 |
| DE | 102010000339 A1 | 8/2011 |
| WO | WO-2007090015 A1 | 8/2007 |
| WO | WO-2008003047 A2 | 1/2008 |
| WO | WO-2008033976 A1 | 3/2008 |

\* cited by examiner

*Primary Examiner* — Jan Christopher Merene
(74) *Attorney, Agent, or Firm* — RatnerPrestia

(57) ABSTRACT

A connecting element for a spinal column stabilization system includes a first attachment section for fixing to a first bone attachment device, a second attachment section for fixing to a second bone attachment device and an at least partially flexible intermediate section. The intermediate section is arranged between the first and the second attachment section and is in the form of a strip-like, winding leaf spring element having at least one recess. A desired spring stiffness is maintained as precisely as possible, especially in the intermediate section independently of possible manufacturing tolerances arising from the manufacturing process. At least one of the two leaf spring element surfaces of the leaf spring element includes at least one stiffness-modifying element. The connecting element may be part of an improved spinal column fixation system and made by an improved method of manufacturing a connecting element.

25 Claims, 9 Drawing Sheets

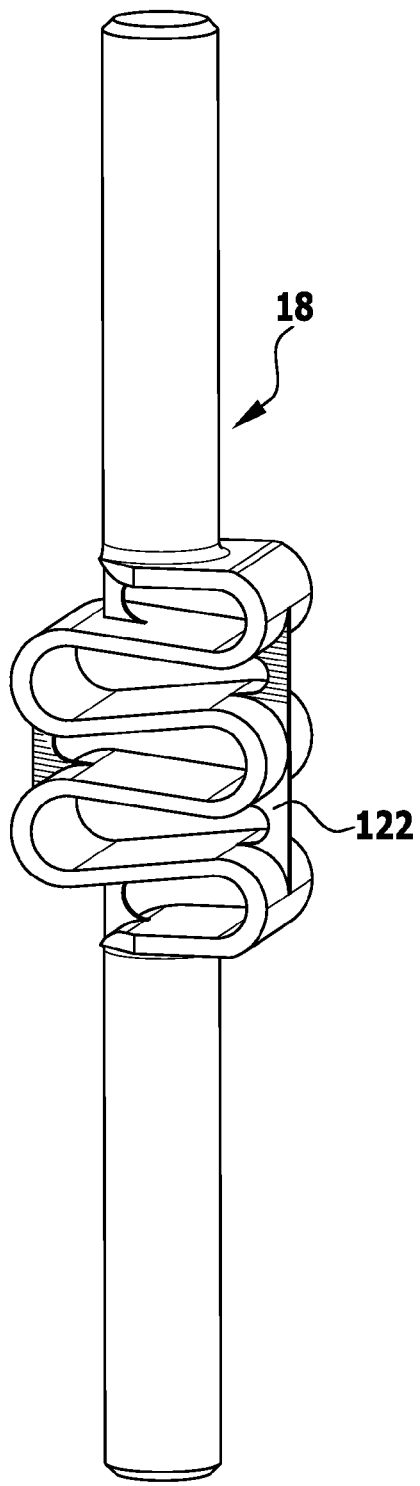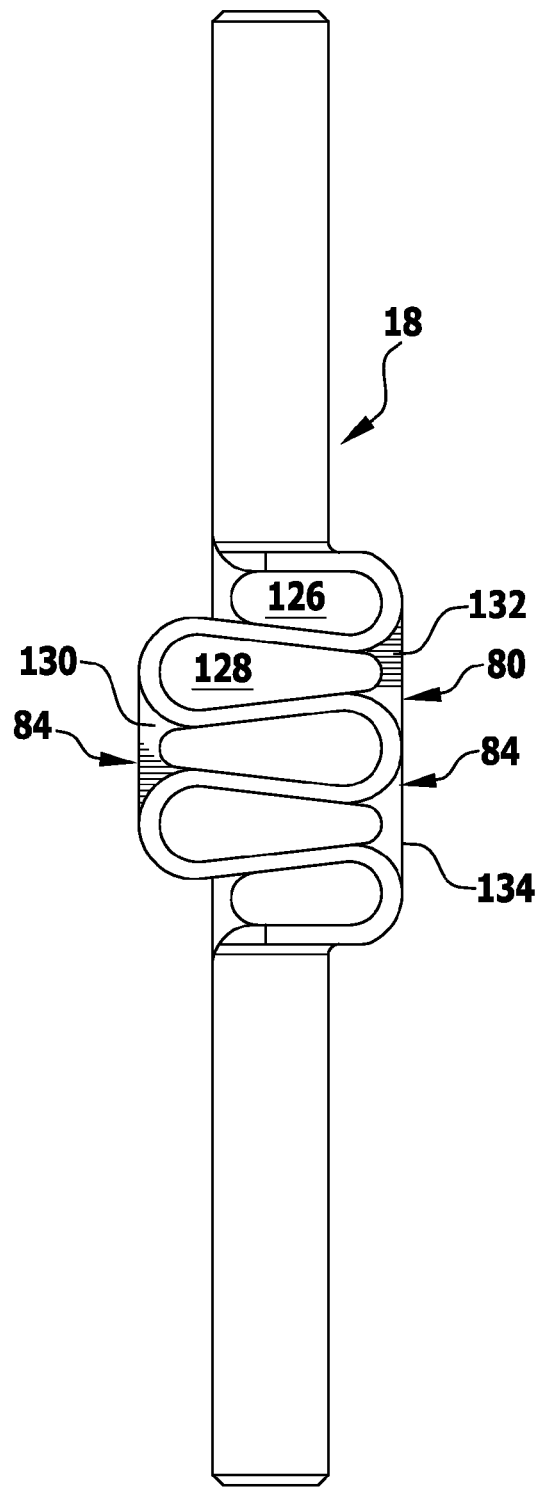

Figure 1:
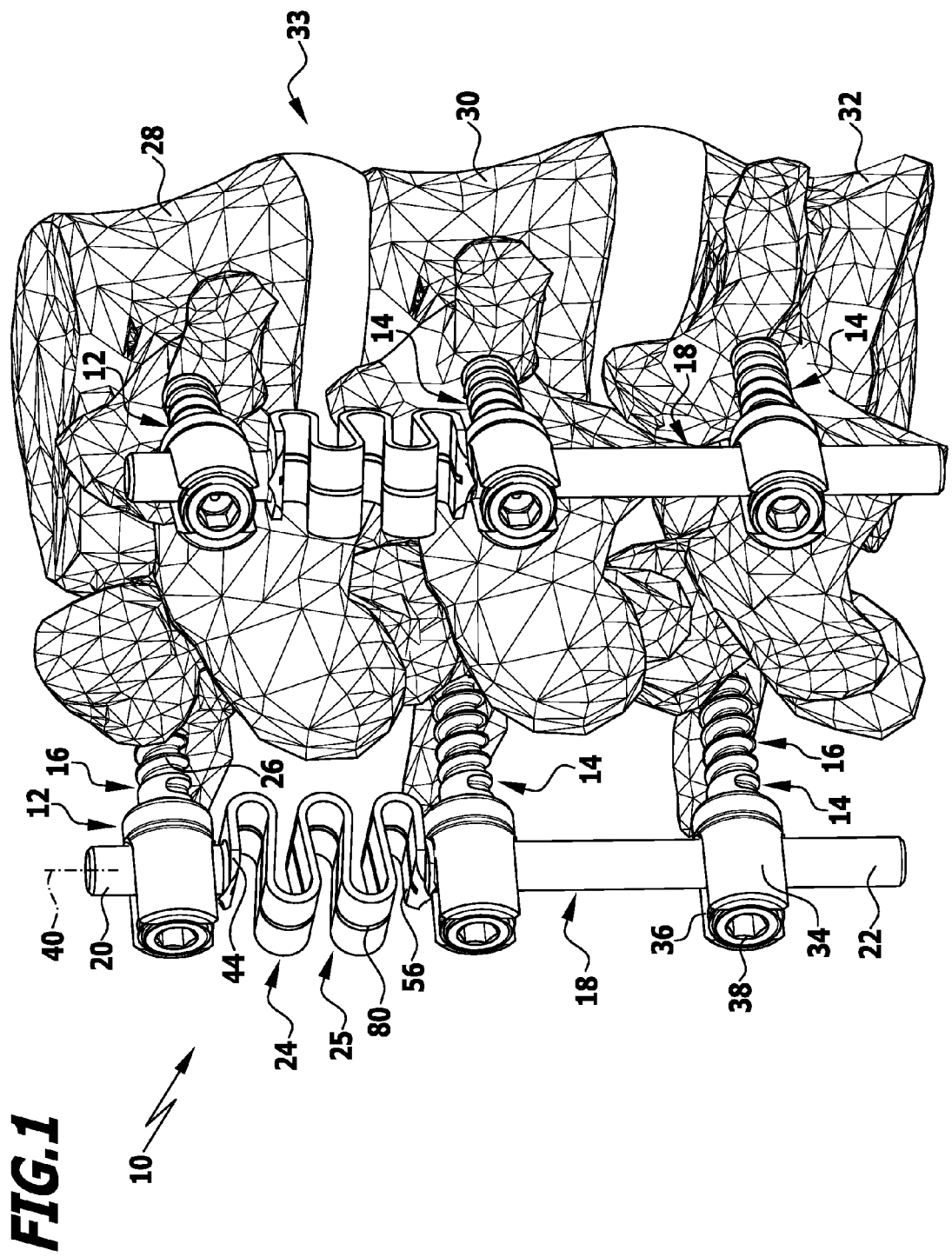

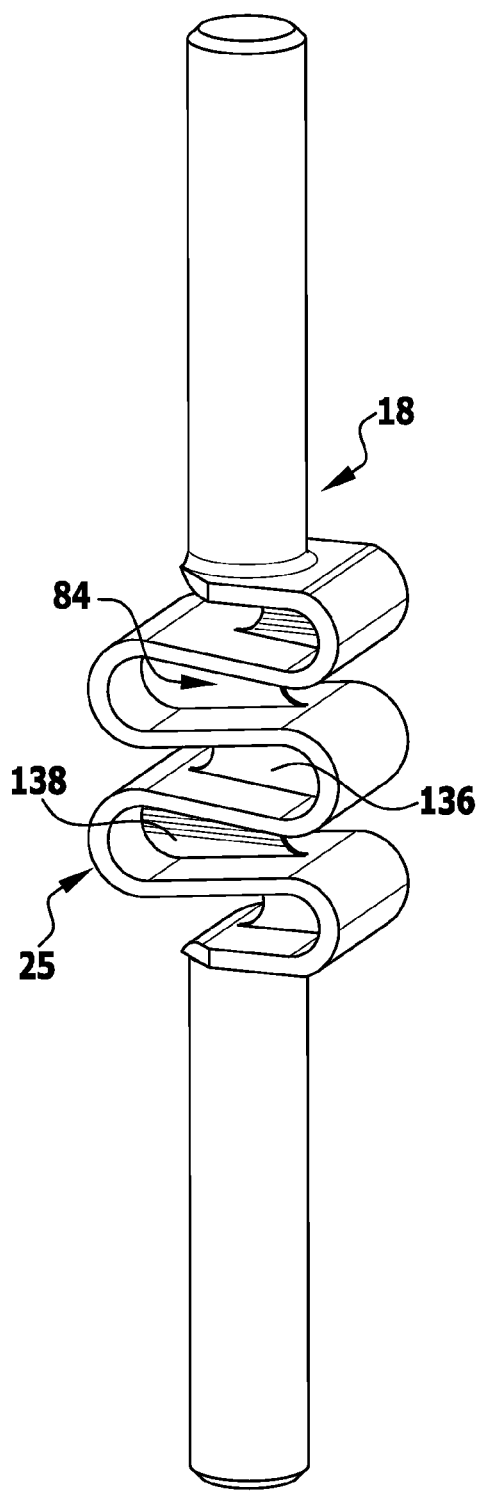
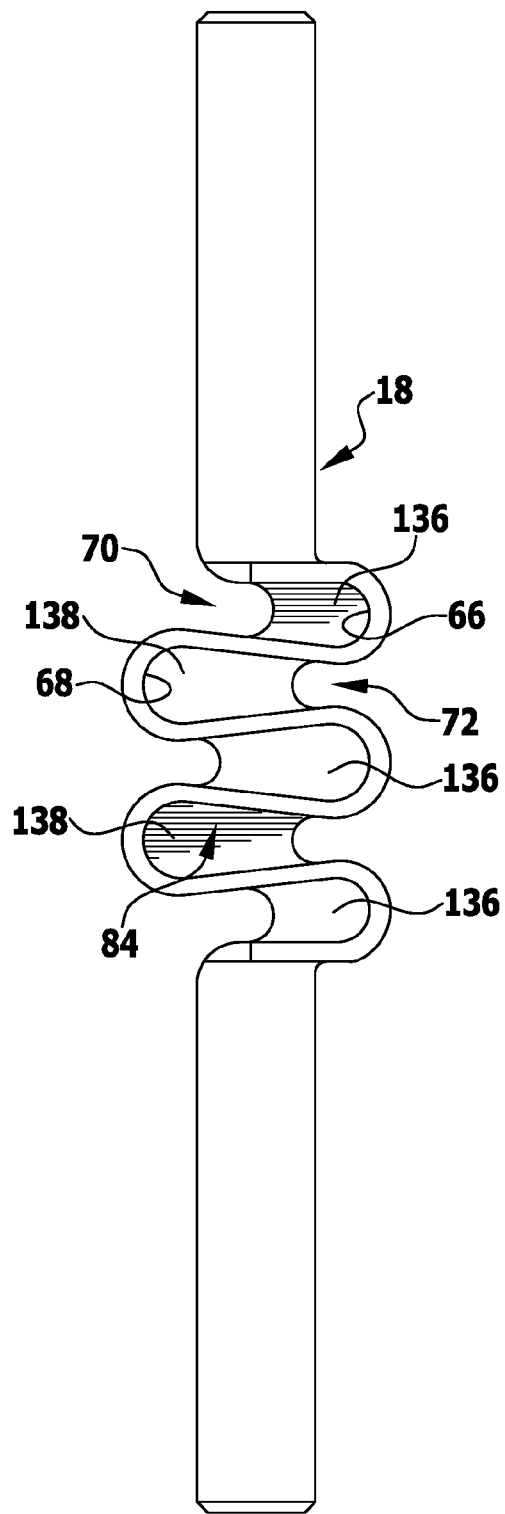

SPINAL COLUMN STABILIZATION SYSTEM, CONNECTING ELEMENT FOR A SPINAL COLUMN STABILIZATION SYSTEM AND METHOD OF MANUFACTURING SUCH A CONNECTING ELEMENT

CROSS-REFERENCE TO RELATED APPLICATIONS

This application claims the benefit of German Patent Application No. 10 2010 060 112.8 filed on Oct. 21, 2010 and German patent Application No. 10 2010 037 665.5 filed on Sep. 20, 2010.

The present disclosure relates to the subject matter disclosed in German application number 10 2010 060 112.8 of Oct. 21, 2010, and in German application number 10 2010 037 665.5 of Sep. 20, 2010, which are incorporated herein by reference in its entirety and for all purposes.

FIELD OF THE INVENTION

The present invention relates to connecting elements for spinal column stabilization systems, and more specifically to a connecting element for a spinal column stabilization system having a first attachment section for fixing to a first bone attachment device, a second attachment section for fixing to a second bone attachment device and an at least partially flexible intermediate section which is arranged or formed between the first and the second attachment section.

Moreover, the present invention relates to spinal column stabilization systems, and more specifically to a spinal column stabilization system comprising at least one first bone attachment device, at least one second bone attachment device and a connecting element, wherein said connecting element comprises a first attachment section for fixing to the at least one first bone attachment device, a second attachment section for fixing to the at least one second bone attachment device and an at least partially flexible intermediate section which is arranged or formed between the first and the second attachment section.

Furthermore, the present invention relates to methods of manufacturing connecting elements for spinal column stabilization systems, and more specifically to a method of manufacturing a connecting element for a spinal column stabilization system having a first attachment section for fixing to a first bone attachment device, a second attachment section for fixing to a second bone attachment device and an at least partially flexible intermediate section which is arranged or formed between the first and the second attachment section.

BACKGROUND OF THE INVENTION

Connecting elements and spinal column stabilization systems of the type described hereinabove are known from US 2006/0184171 A1 for example. In the case of the known connecting elements, the desired stiffness thereof and especially that of the intermediate section thereof, depends on the prevailing manufacturing tolerances. Furthermore, it is not possible with the known connecting elements for the stiffness of the intermediate section to be specifically set within small ranges during the manufacturing process nor is it possible to adjust it subsequently. Such a "fine adjustment" process would, however, be very advantageous. Moreover, thin-walled springy components are difficult to manufacture whereby in particular, a high surface quality can only be attained with great difficulty using material-removing machining processes. Again, the consequences thereof are unavoidable manufacturing tolerances. Leaf spring elements can of course be easily manufactured by means of wire erosion methods for example, but nevertheless, the structure of the eroded material at the surface may then be changed in a disadvantageous manner. Moreover, residual matter from the eroded wire usually has to be removed by chemical methods such as an etching process for example, this in turn leading to ill-defined dimensions and surfaces. And on top of this, it is not possible for the stiffness of the known connecting elements to be varied, not even intra-operatively should this be required.

SUMMARY OF THE INVENTION

In a first aspect of the invention a connecting element for a spinal column stabilization system comprises a first attachment section for fixing to a first bone attachment device, a second attachment section for fixing to a second bone attachment device and an at least partially flexible intermediate section which is arranged or formed between the first and the second attachment section. Said intermediate section is in the form of a strip-like, winding leaf spring element and comprises at least one recess which is open to the side in a direction transverse to a longitudinal axis defined by the intermediate section. At least one of the two leaf spring element surfaces of the leaf spring element comprises at least one stiffness-modifying element.

In a second aspect of the invention a spinal column stabilization system comprises at least one first bone attachment device, at least one second bone attachment device and a connecting element. Said connecting element comprises a first attachment section for fixing to the at least one first bone attachment device, a second bone attachment section for fixing to the at least one second bone attachment device and an at least partially flexible intermediate section that is arranged or formed between the first and the second attachment section. Said intermediate section is in the form of a strip-like, winding leaf spring element and comprises at least one recess which is open to the side in a direction transverse to a longitudinal axis defined by the intermediate section. At least one of the two leaf spring element surfaces of the leaf spring element comprises at least one stiffness-modifying element.

In a third aspect of the invention a method is provided of manufacturing a connecting element for a spinal column stabilization system comprising a first attachment section for fixing to a first bone attachment device, a second bone attachment section for fixing to a second bone attachment device and an at least partially flexible intermediate section that is arranged or formed between the first and the second attachment section. Said intermediate section is in the form of a strip-like, winding leaf spring element and comprises at least one recess which is open to the side in a direction transverse to a longitudinal axis defined by the intermediate section. At least one stiffness-modifying element is formed on at least one of the two leaf spring element surfaces of the leaf spring element.

BRIEF DESCRIPTION OF THE DRAWING FIGURES

Figure 2:
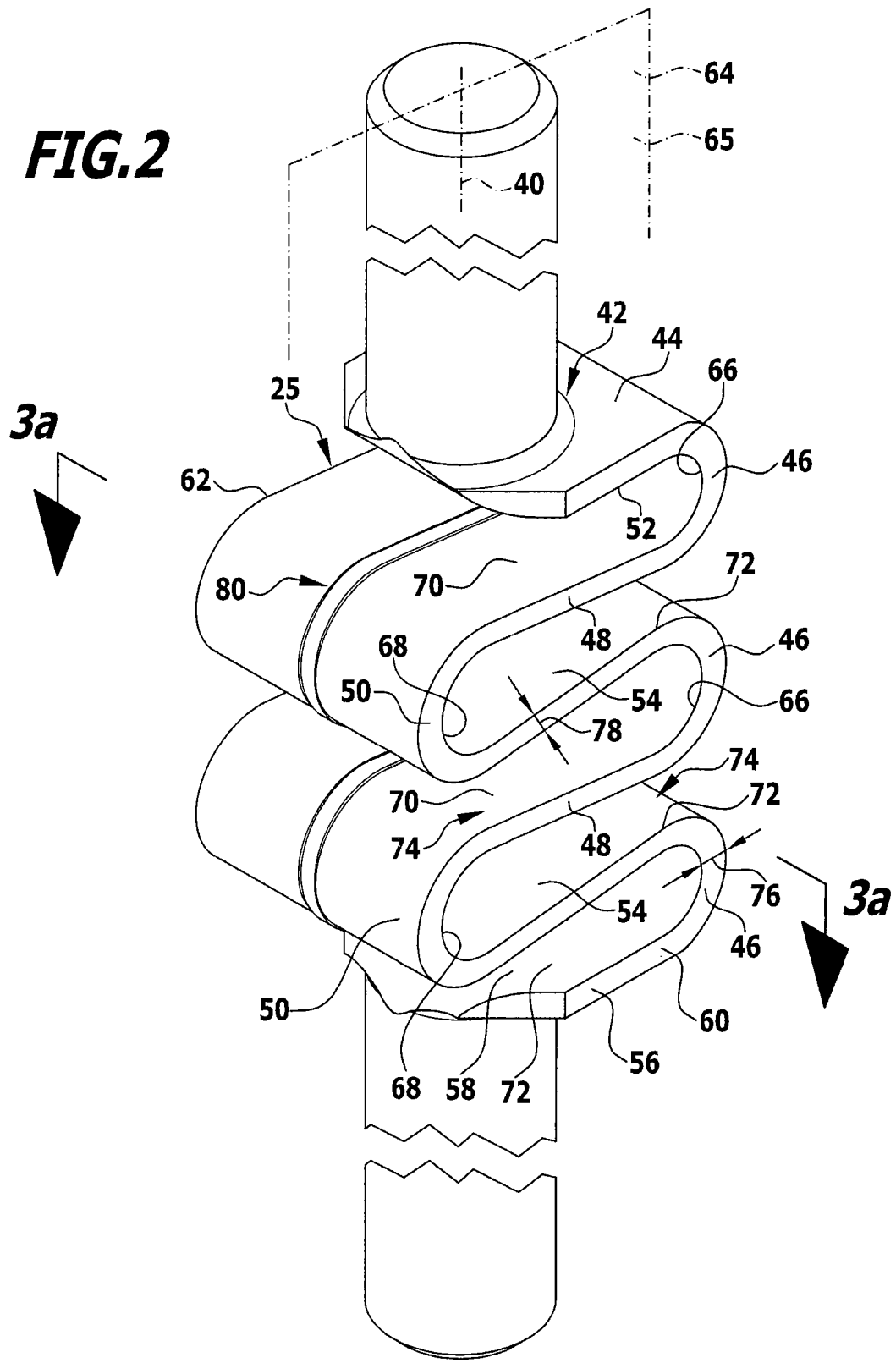
Figure 3A:
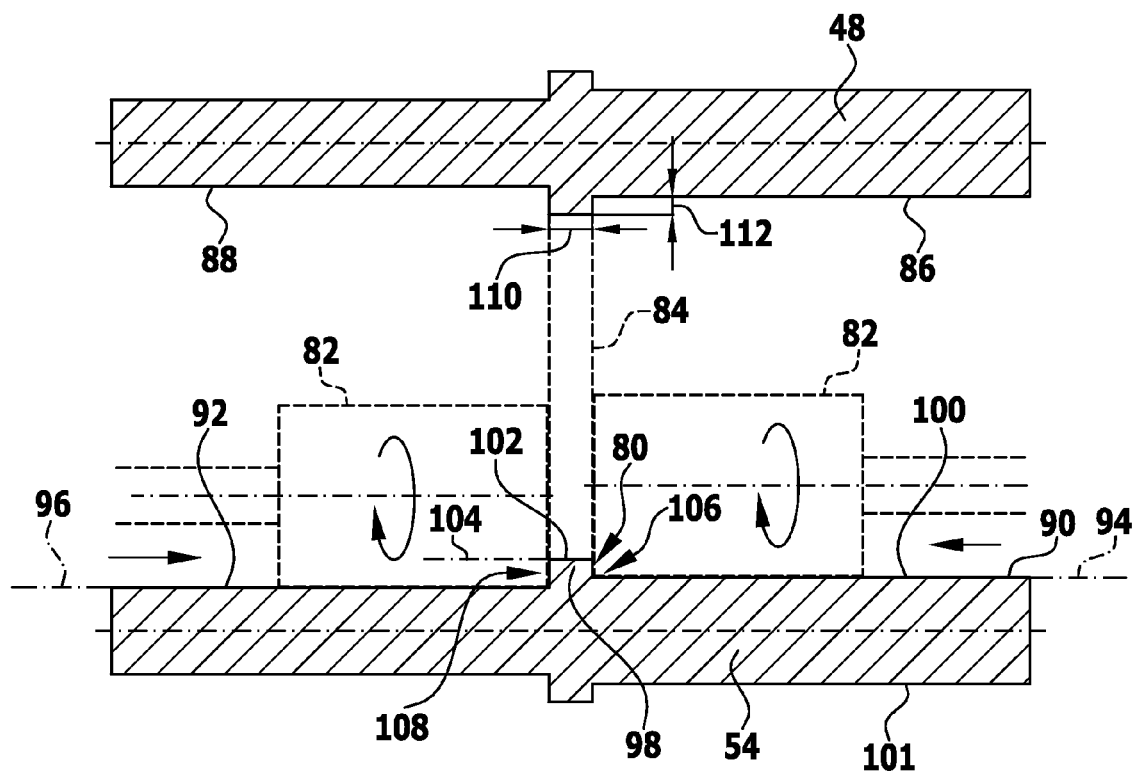
Figure 3B:
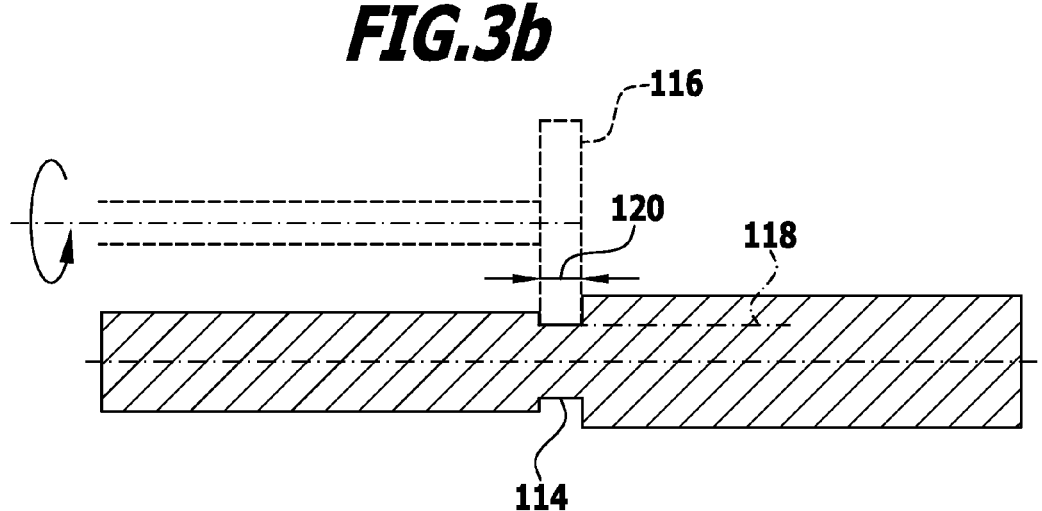
Figure 4A:
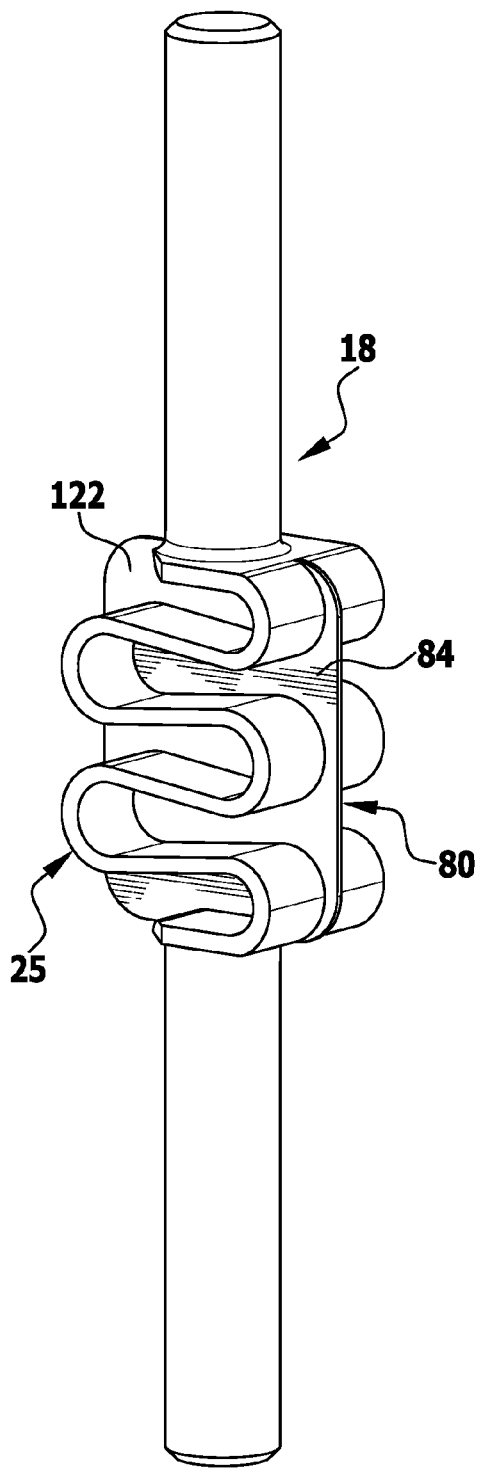
Figure 4B:
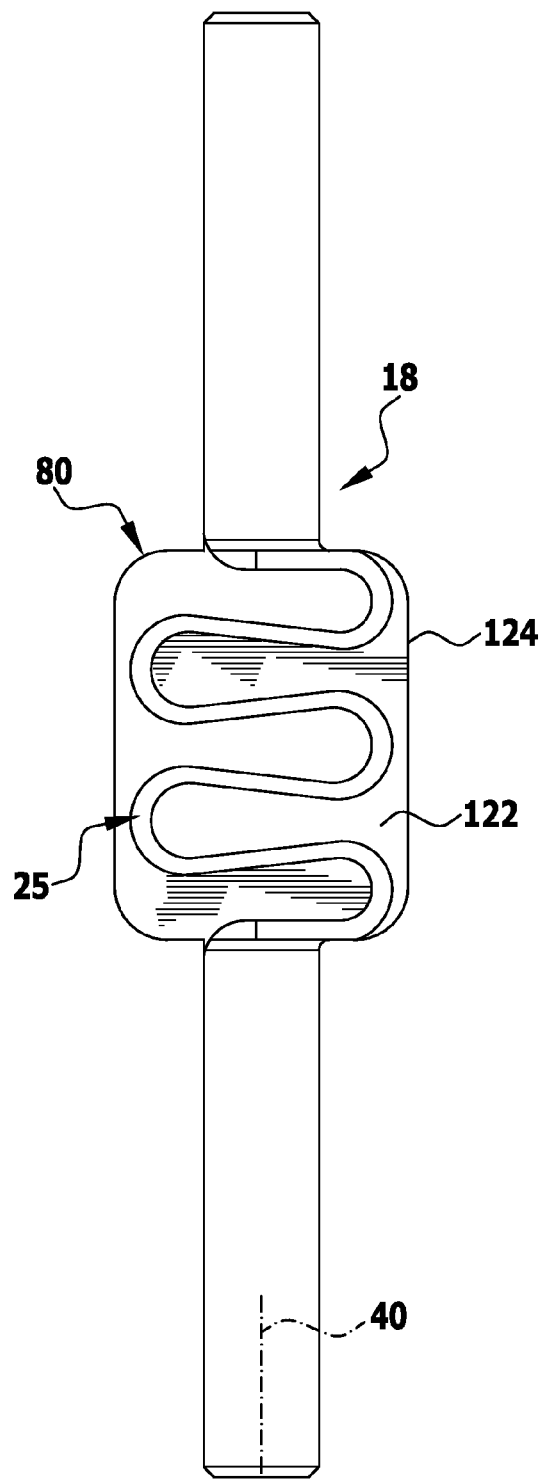
Figure 5A:
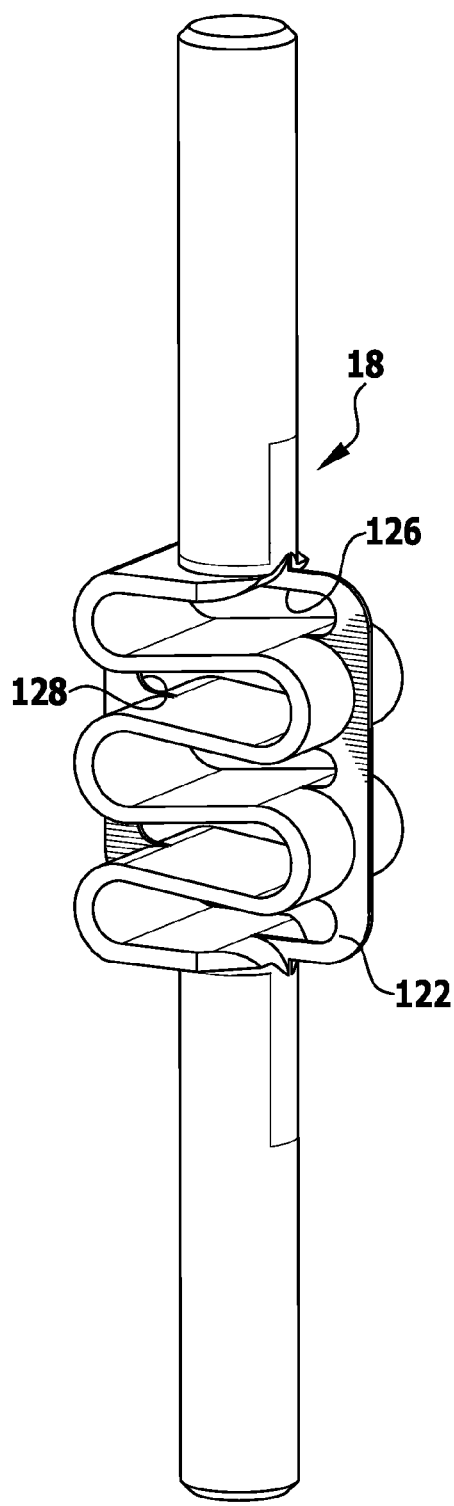
Figure 5B:
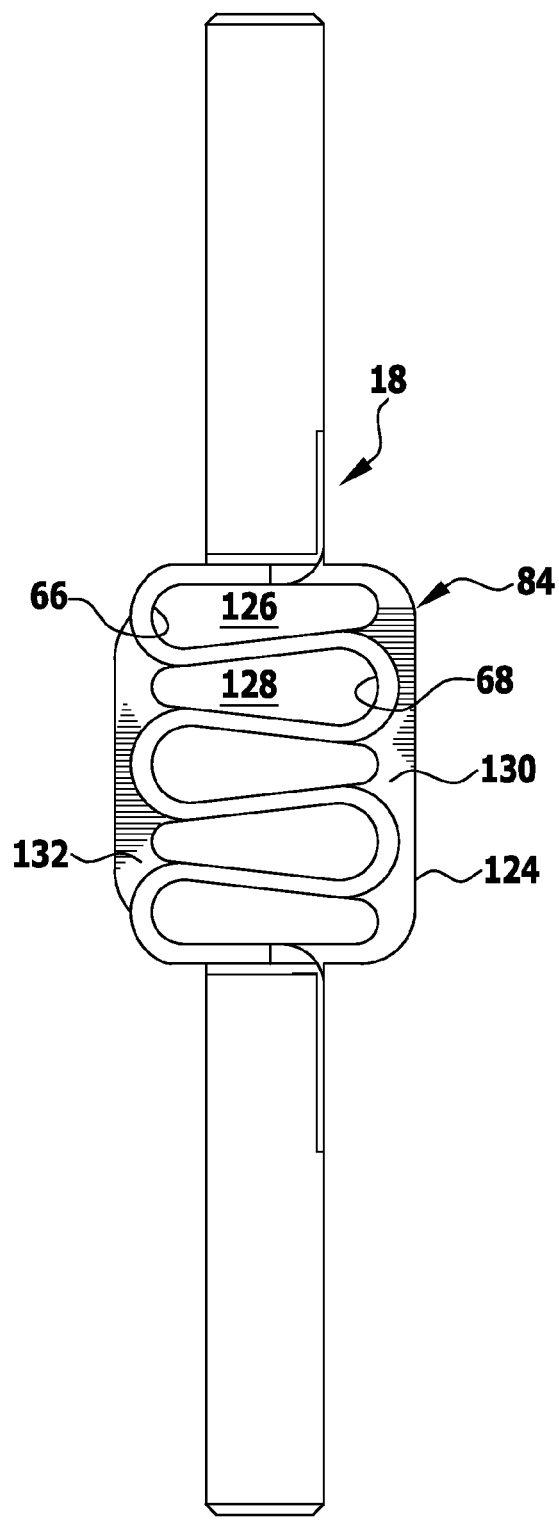
Figure 8A:
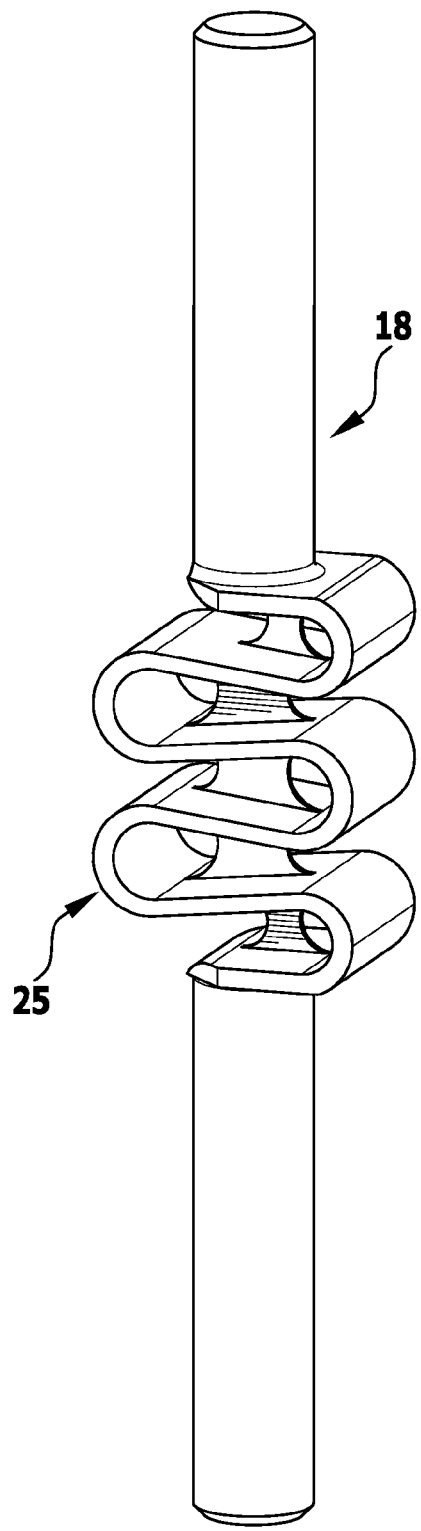
Figure 8B:
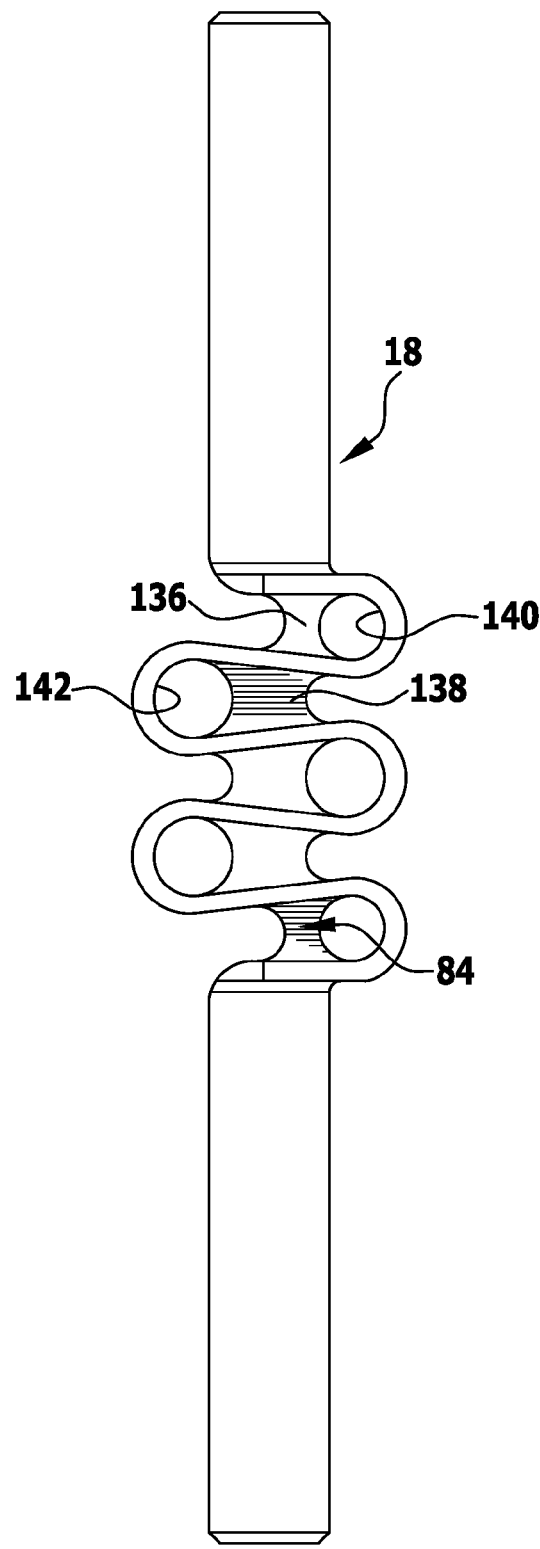

The foregoing summary and the following description may be better understood in conjunction with the drawing figures, of which:

FIG. 1: shows a schematic overall view of a spinal column stabilization system fixed to a spinal column;

FIG. 2: a perspective schematic view of a connecting element of the spinal column stabilization system depicted in FIG. 1;

FIG. 3a: a schematic sectional view along the line 3a-3a in FIG. 2;

FIG. 3b: a sectional view analogous to FIG. 3a of a further exemplary embodiment of a connecting element;

FIG. 4a: a perspective view of a further exemplary embodiment of a connecting element;

FIG. 4b: a side view of the connecting element depicted in FIG. 4a;

FIG. 5a: a perspective view of a further exemplary embodiment of a connecting element;

FIG. 5b: a side view of the connecting element depicted in FIG. 5a;

FIG. 6a: a perspective view of a further exemplary embodiment of a connecting element;

FIG. 6b: a side view of the connecting element depicted in FIG. 6a;

FIG. 7a: a perspective view of a further exemplary embodiment of a connecting element;

FIG. 7b: a side view of the connecting element depicted in FIG. 7a;

FIG. 8a: a perspective view of a further exemplary embodiment of a connecting element;

FIG. 8b: a side view of the connecting element depicted in FIG. 8a; and

Figure 9:
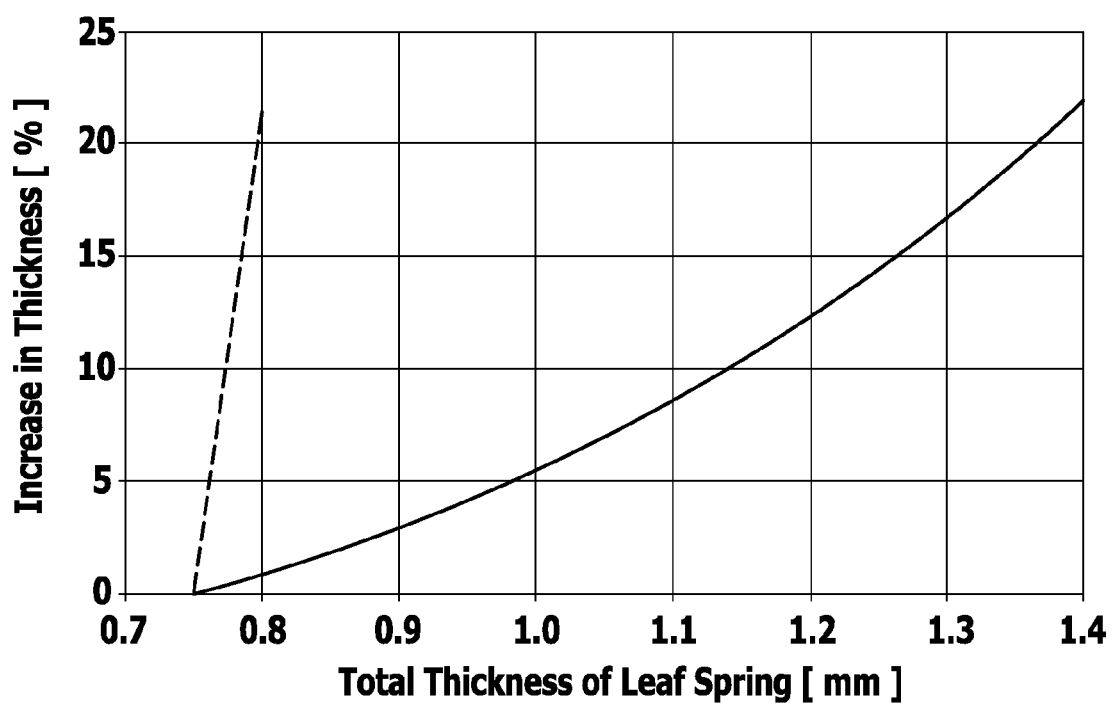

FIG. 9: an exemplary schematic diagram depicting the increase in stiffness of the intermediate section in dependence on the wall thickness of the leaf spring element, namely with and without a stiffness-modifying element in the form of a projection.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to connecting element for a spinal column stabilization system comprising a first attachment section for fixing to a first bone attachment device, a second attachment section for fixing to a second bone attachment device and an at least partially flexible intermediate section which is arranged or formed between the first and the second attachment section, which said intermediate section is in the form of a strip-like, winding leaf spring element and comprises at least one recess which is open to the side in a direction transverse to a longitudinal axis defined by the intermediate section, wherein at least one of the two leaf spring element surfaces of the leaf spring element comprises at least one stiffness-modifying element.

The at least one stiffness-modifying element can be used, in particular, for specifically correcting the spring stiffness of the intermediate section when it deviates from the desired value as a result of manufacturing tolerances occurring in the production of the intermediate section. This can be effected, in particular, directly during the production process, i.e. when manufacturing the connecting element, or else it can be done perhaps at a later time intra-operatively by the operating surgeon for example. Self evidently, both leaf spring element surfaces of the leaf spring element may comprise one or more stiffness-modifying elements. These can, in particular, define a common longitudinal direction when parallel to each other or even when spaced from each other or they may be arranged or formed such that they are mutually laterally offset.

The connecting element can be produced in a particularly simple and stable manner, if the at least one stiffness-modifying element and the leaf spring element are formed in one piece manner.

The production of the connecting element can be further simplified, if the at least one stiffness-modifying element is formed in strip-like manner. Preferably, the stiffness-modifying element extends in a longitudinal direction defined by the leaf spring element. However, it would also be conceivable for the at least one stiffness-modifying element to be formed in a direction transverse to this longitudinal direction.

Since manufacturing tolerances typically affect the leaf spring element as a whole, it is expedient for the at least one stiffness-modifying element to extend over the entire length of the leaf spring element. For example, it can reach from one end to the other end of the leaf spring element in the form of a longitudinal strip, i.e. extend between the two attachment sections over the entire length of the intermediate section. Optionally, both surfaces of the leaf spring element may comprise such a stiffness-modifying element.

It is advantageous, if both leaf spring element surfaces of the leaf spring element each comprise at least one stiffness-modifying element. These may be identical or could optionally be formed differently in dependence on the respective surface of the leaf spring element.

In accordance with one preferred embodiment of the invention, provision may be made for the at least one stiffness-modifying element to be in the form of a stiffening projection which protrudes from one of the two surfaces of the leaf spring element. Such a stiffening projection can be produced using a particularly simple manufacturing technique, if the recess in the leaf spring element is prepared using a machining process from the two opposite sides thereof by means of face or milling cutters whereby a partition wall, which separates the indentations being formed from the two sides, is initially allowed to remain. Such a partition wall and a stiffening projection that may still be in place after partial removal of the partition wall, can be left in their complete state but they could also be partly removed later, whereby the stiffness of the leaf spring element can be set in a desired and specific manner in dependence on the remaining stiffening projection, i.e. in dependence on the size and/or extent and/or the thickness thereof or it can be adjusted later where necessary. In particular, should the stiffness resulting from the production process be too low, then it can be increased in a simple and highly precise manner with the aid of the stiffening projection.

In order to reduce a somewhat excessive stiffness of the intermediate section at the end of the manufacturing process should this be required, it can be advantageous if the at least one stiffness-modifying element is in the form of a stiffening groove which extends from one of the two surfaces of the leaf spring element into the leaf spring element. Such a stiffening groove can be produced in a simple manner with the aid of a T-type milling tool for example. In like manner to the stiffening projection, a stiffening groove can extend in the longitudinal direction of the leaf spring element or else transversely thereto where necessary. Just one stiffening groove may be provided or else a plurality thereof may be provided, these being formed or arranged such as to be spaced one behind the other and/or laterally offset with respect to each other.

Advantageously, the at least one stiffness-modifying element extends between two mutually facing surface sections of one of the two surfaces of the leaf spring element. In other words, the stiffness-modifying element can be arranged in the region of a recess for example. It can, in particular, be formed in a fin-like manner or be in the form of a kind of "webbing" and thus increase the stiffness of a loop of the leaf spring element in specific manner.

It is particularly advantageous, if the at least one stiffness-modifying element is arranged in the region of the at least one recess. In particular, it can be arranged and formed to be of a size such that it completely closes the recess in the direction transverse to the longitudinal axis of the connecting element. However, the thickness of the stiffening element may only amount to a fraction of the width of the intermediate section within this region. In particular, the thickness of the stiffness-modifying element can be smaller than the thickness of the leaf spring element.

The connecting element can be manufactured in a particularly simple manner, if the connecting element is formed such that it is mirror-symmetrical or substantially mirror-symmetrical with respect to a mirror plane. Substantially mirror-symmetrical means in particular that, due to the manufacturing tolerances occurring during the production of the intermediate section from a solid material, a continuous leaf spring element surface cannot be produced, but rather, it may have at least one single-step shoulder as the result of a slightly displaced milling device or other material-removing machining tool.

The stability and also the bending properties of the connecting element can be adjusted in a particularly simple and highly precise manner, if the mirror plane contains a longitudinal axis defined by the connecting element.

The connecting element can be used in a particular outstanding manner as a replacement for a straight, rod-like connecting element, if the longitudinal axis defines longitudinal axes of the attachment sections.

The connecting element can be manufactured in a particularly simple manner and the stiffness thereof can also be easily adjusted, if the at least one stiffness-modifying element is formed such that it is mirror-symmetrical or substantially mirror-symmetrical with respect to the mirror plane. As described above for example, it can be in the form of a partition wall which is formed mirror-symmetrically with respect to the mirror plane by a special manufacturing process.

Furthermore, it can be advantageous if the leaf spring element has differing thicknesses on the one side and the other side of the at least one stiffness-modifying element. This arrangement makes it possible for the demands on the manufacturing tolerances entailed in the production of the intermediate section to be lowered somewhat. The production of the connecting element is simplified in this way, since manufacturing tolerances affecting the stiffness of the intermediate section can be specifically corrected by an appropriate design of the stiffness-modifying element. In particular, it is also possible thereby to manufacture the leaf spring element using a milling process by means of two oppositely directed milling tools which initially form the recess as two indentations which are separated from each other by a partition wall. The wall thicknesses of the leaf spring element can thereby vary due to manufacturing tolerances especially on the one side and the other side of the partition wall, i.e. on the one side and the other side of the stiffness-modifying element.

In accordance with a further preferred embodiment of the invention, provision may be made for the connecting element to comprise at least one through hole which extends transversely relative to a longitudinal axis defined by the connecting element and which is bounded at least in sections by the at least one stiffness-modifying element. In dependence on the size of the through hole, a change in the stiffness of the leaf spring element that has been caused by the stiffness-modifying element can be compensated in a specific manner. In particular, it is conceivable for the stiffness-modifying element to completely surround the through hole, and especially for it to border on the through hole in its entirety.

For the purposes of forming connecting webs on the leaf spring element for example, it can be advantageous for the through hole to be at least partly bounded by the leaf spring element. In particular, it can then also be partly bounded by the stiffness-modifying element.

It is advantageous, if the thickness of the at least one stiffness-modifying element in a direction transverse or substantially transverse to a longitudinal axis defined by the connecting element corresponds at most to approximately the thickness of the leaf spring element. The thickness of the stiffness-modifying element can serve in particular for adjusting the stiffness of the intermediate section, for example, for compensating for manufacturing tolerances. Since the stiffness should be determined primarily by the leaf spring element, it is expedient if the thickness of the stiffness-modifying element is selected in the given manner.

Preferably, the thickness of the at least one stiffness-modifying element lies in a range extending from approximately 0.2 mm up to approximately 0.6 mm. It is expedient, if it lies in a range from approximately 0.3 mm up to approximately 0.5 mm.

Expediently, the thickness of the leaf spring element lies in a range extending from approximately 0.5 mm up to approximately 1.5 mm. Preferably, the thickness of the leaf spring element lies in a range extending from approximately 0.5 mm up to approximately 0.9 mm. It preferably lies in a range from approximately 0.6 mm up to approximately 0.8 mm. In particular, the thickness of the leaf spring element may vary. For example, curved sections of the leaf spring element can be thicker than straight sections thereof. In particular, the thickness of a curved section of the leaf spring element can lie in a range extending from approximately 0.7 up to approximately 1.2 mm. For example, it can have a value of 0.975 mm. In particular, the thickness of a straight section of the leaf spring element can lie in a range extending from approximately 0.5 up to approximately 0.9 mm. For example, it can have a value of 0.775 mm.

In accordance with a further preferred embodiment of the invention, provision may be made for at least one of the two surfaces of the leaf spring element to comprise at least two step-like shoulders so that the at least one of the two surfaces of the leaf spring element comprises at least two, and preferably three flat, mutually parallel leaf spring element surface sections. Leaf spring element surfaces formed in this manner can, for example, comprise a strip-like projection which could also be referred to as a rib and serves to form a stiffness-modifying element, or it could however be a stiffening groove which likewise separates two surface sections of the leaf spring from each other. The step-like shoulders on the surfaces of the leaf spring element can, in dependence on the height of the respective shoulders, be deliberately used for specifically readjusting the stiffness of the intermediate section to a desired value when it deviates from the desired value.

Preferably, the at least one recess is open to the side in two mutually opposite directions. This can be achieved for example in that the recess is prepared by means of two milling devices operating in mutually facing directions in such a manner that a partition wall remains between the two thus formed indentations. Optionally, the partition wall can also be partly removed.

For the purposes of increasing the stability of the connecting element, it is expedient for it to be formed in one piece manner.

Surfaces of high quality can then be obtained especially when the connecting element is made from a solid material by means of a material-removing machining process. The fatigue strength of the connecting element is dependent in particular on the quality of the surfaces of the connecting element. This can be increased if necessary after a material-removing machining process by means of a subsequent surface treatment.

It is expedient, if the connecting element is made from a metallic material or a synthetic material. Depending upon the stiffness required, one or the other of these materials can be selected for the production of the connecting element. In particular, practically any degrees of stiffness can be achieved by appropriate choice of the material. They preferably lie in a range from approximately 30 N/mm to 150 N/mm.

Preferably, the metallic material is titanium, a titanium alloy or a cobalt chromium alloy or it contains the aforesaid materials. In particular, it is a biocompatible metallic material.

Expediently, the synthetic material is polyetheretherketone (PEEK) or carbon fibre reinforced polyetheretherketone (PEEK) or it contains the aforesaid materials. In particular, the aforesaid materials excel due to their high biocompatibility.

The present invention also relates to a spinal column stabilization system comprising at least one first bone attachment device, at least one second bone attachment device and a connecting element, which connecting element comprises a first attachment section for fixing to the at least one first bone attachment device, a second bone attachment section for fixing to the at least one second bone attachment device and an at least partially flexible intermediate section that is arranged or formed between the first and the second attachment section, which intermediate section is in the form of a strip-like, winding leaf spring element and comprises at least one recess which is open to the side in a direction transverse to a longitudinal axis defined by the intermediate section, wherein at least one of the two leaf spring element surfaces of the leaf spring element comprises at least one stiffness-modifying element.

A connecting element of the spinal column stabilization system which is improved in such a manner incorporates the advantages that have already been described above and it thus also serves to provide an improvement in the spinal column stabilization system taken as a whole.

Furthermore, it is expedient if the connecting element of the spinal column stabilization system is in the form of one of the preferred embodiments described above. The spinal column stabilization system as a whole then also has the advantages of the improved connecting elements.

The invention also relates to a method of manufacturing a connecting element for a spinal column stabilization system comprising a first attachment section for fixing to a first bone attachment device, a second bone attachment section for fixing to a second bone attachment device and an at least partially flexible intermediate section that is arranged or formed between the first and the second attachment section, which intermediate section is in the form of a strip-like, winding leaf spring element and comprises at least one recess which is open to the side in a direction transverse to a longitudinal axis defined by the intermediate section, wherein at least one stiffness-modifying element is formed on at least one of the two leaf spring element surfaces of the leaf spring element.

Due to the provision of the at least one stiffness-modifying element, manufacturing tolerances occurring during the process of manufacturing the connecting element can, for example, be compensated for in a desired manner at the end of the manufacturing process or possibly even later, for example intra-operatively by an operating surgeon. The provision of the at least one stiffness-modifying element thus makes it possible for deviations from the desired stiffness of a leaf spring element due to manufacturing tolerances arising in the production of the intermediate section to be corrected in a specific manner.

The connecting element can be manufactured in a particularly simple manner, if the leaf spring element is made from a solid material by a material-removing machining process. In particular, leaf spring element surfaces of high quality can be formed in such a way, this thereby contributing to an increase in the overall fatigue strength of the connecting element.

It is advantageous furthermore, if the first and/or the second attachment section are made from a solid material by a material-removing machining process. Thus in particular, the entire connecting element can be made of a solid material and is thus producible in one piece manner where necessary.

The connecting element can be manufactured with particularly high quality and high surface quality in a simple manner in that it is subjected to a material-removing process that is effected by a milling process. For example, recesses can be produced in the manner described above using face or milling cutters, and stiffness-modifying elements in the form of grooves can be produced by means of T-type milling tools.

In accordance with a preferred variant of the method in accordance with the invention, provision may be made for the at least one recess to be formed by milling from both sides in directions oriented towards each other that are transverse to a longitudinal axis defined by the connecting element and for the overall milling depth in a direction transverse to the longitudinal axis to be smaller than the thickness of the connecting element in a milling direction transverse to the longitudinal axis so that a partitioning element is formed which separates the two milled-out indentations from each other. The sum of the depths of the two indentations is thus smaller than the thickness of the connecting element in a milling direction transverse to the longitudinal axis. The partitioning element can thus be formed, in particular, in the manner of a "webbing" which closes the recesses laterally and separates the milled-out indentations from each other. In particular, the partitioning element can protrude laterally beyond the turns of the leaf spring element and thus delimit an outer contour of the connecting element of the intermediate section in a cross sectional view.

The partitioning element can be formed in a particularly simple manner, if it is in the form of a wall. For example, the stiffness of the leaf spring element can be adjusted specifically by means of the wall thickness of the partitioning element.

In order in particular to subsequently adjust the stiffness of the connecting element in a desired manner, the partitioning element can be partly removed. For example, it can be broken through or be almost completely removed for the purposes of forming a strip-like projection.

The partitioning element can be partly removed in a particularly simple manner by boring, milling or cutting. In particular, the partial removal thereof by a cutting process can also be realized intra-operatively when necessary. For example, the connecting element can be delivered in the first place with a completely formed partition wall so that this can then be removed to the desired extent by an operating surgeon for specially matching it to the physiological needs of a patient for example.

Advantageously, the partitioning element is partly broken through in a direction transverse to the longitudinal axis. The stiffness of the leaf spring element can be lowered specifically in this way.

A spinal column stabilization system bearing the general reference symbol 10 is illustrated schematically in FIG. 1. It comprises first bone attachment devices 12 and second bone attachment devices 14 which are all in the form of identical bone screws 16 in the exemplary embodiment that is schematically illustrated in FIG. 1, although they could also be of different constructions. Furthermore, the spinal column stabilization system 10 comprises substantially rod-like connecting elements 18 which comprise a first attachment section 20 for fixing to a bone screw 16, a second attachment section 22 for fixing to two bone screws 16 and an at least partially flexible intermediate section 24 in the form of a leaf spring element 25 that is arranged or formed between the first and the second attachment sections 20, 22.

The bone screws 16 each comprise a bone anchorage section 26 having a bone thread for anchorage in a bone, for example, in one of the vertebrae 28, 30 and 32 of a spinal column 33 that are illustrated schematically in FIG. 1. Moreover, each bone screw 16 comprises a retaining section 34 in the form of a yoke which comprises an attachment section seating 36 for one of the attachment sections 20, 22 of a connecting element 18 and is mounted on the bone anchorage section 26 in articulated manner in an adjustment position. An attachment section 20, 22 inserted into the attachment section seating 36 can be fixedly clamped in the implantation position thereof by means of a clamping screw 38. In addition, a relative positioning between the bone anchorage section 26 and the retaining section 34 is preferably permanently established by fixing the attachment section 20, 22 to the retaining section 34.

The attachment sections 20, 22 are each in the form of a round rod-like member and thus have a circular cross section. They are formed in one piece with the intermediate section 24. Preferably, as is the case in the exemplary embodiment of a connecting element 18 illustrated in FIGS. 1 and 2, the attachment sections 20 and 22 define a common longitudinal axis 40 which also defines the longitudinal axis of the intermediate section 24.

The intermediate section 24 is formed onto a first end of the attachment section 20 and it is in the form of a substantially flat, parallelepipedal end plate 44 in the transition region 42 to the attachment section 20. A curved section 46 extending transversely relative to the longitudinal axis 40 adjoins the long side of the end plate. It extends over an angular range of somewhat more than 180°. Adjoining the curved section 46, there is a flat planar section 48 which in its turn changes into a curved section 50 that is likewise convexly curved in a direction away from the longitudinal axis 40. The curved sections 46 and 50 however are oriented in mutually opposite directions. An end face 52 of the end plate 44 facing in the direction of the second attachment section 22 is inclined somewhat with respect to the planar section 48. Adjoining the curved section 50, there is another planar section 54 which is likewise somewhat inclined with respect to the end face 52. The serpentine contour of the intermediate section 24 is continued by means of a further curved section 46, a further planar section 48 adjoined thereto, an adjoining curved section 50, a planar section 54 that is adjoined thereto and a final curved section 46 which is adjoined to the latter section 54 and merges into an end plate 56 that is formed in correspondence with the end plate 44 and which comprises an end face 58 that faces toward the first attachment section 20 and is likewise somewhat inclined relative to the planar sections 54 although it runs in parallel with the end face 52.

A stiffness of the intermediate section 24 lies within a range from approximately 30 N/mm to approximately 150 N/mm in dependence upon the choice of material from which the connecting element 18 is made. The intermediate section 24 is formed from an overall substantially flat leaf spring material or it is formed from a solid material by a material-removing machining process such as a milling process for example, or by means of an erosion process. In a basic position in which no external forces are effective on the intermediate section 24, the intermediate section 24 comprises two mutually parallel side faces 60 and 62 which face in opposite directions transverse to the longitudinal axis 40. In addition, these side faces run in parallel with a plane of symmetry 64 of the connecting element 18 that contains the longitudinal axis 40 and defines a mirror plane 54.

A total of five recesses 66, 68 are formed as a result of the serpentine configuration of the intermediate section 24 in the exemplary embodiment illustrated in the Figures, whereby the three recesses 66 are oriented in the same direction as that in which the convexly curved sections 50 are oriented. The two recesses 68 are oriented in the opposite direction, i.e. in the direction in which the convex curved sections 46 are oriented. Each of the recesses 66, 68 defines a respective entrance opening 70 and 72 which is located opposite a respective curved section 46 and 50 and is oriented in the respectively opposite direction. Each recess 66, 68 is bounded by two planar sections 48 and 54 which run towards one another in the direction of the respective entrance opening 70, 72, so that the cross section of the respective approximately drop-shaped recesses 66, 68 increases from the respective entrance opening 70 and 72 in the direction of the curved sections 46, 50 which further bound the recesses 66, 68. Each entrance opening 70, 72 thus defines a narrow region 74. The respective recesses 66, 68 are thus open to the side in a direction transverse to the longitudinal axis 40.

A thickness 76 of the intermediate section 24 in the region of the curved sections 46, 50 is greater than that in the region of the planar sections 48, 54. The thickness 76 amounts to approximately 1.1 times to approximately 1.5 times the thickness 78, preferably to approximately 1.3 times to approximately 1.35 times. In the case of the exemplary embodiment illustrated in the Figures, the thickness 76 amounts to approximately 0.8 mm, the thickness 78 to approximately 0.6 mm. The thickness 76 preferably lies in a range extending from approximately 0.5 mm up to approximately 1.5 mm. It is preferred if it lies in a range from approximately 0.7 mm up to approximately 1.1 mm. It is further preferred if it lies in a range from approximately 0.7 mm up to approximately 0.9 mm. For example, the thickness 76 can have a value of approximately 0.975 mm. The thickness 78 lies preferably in a range from approximately 0.5 mm up to 1.5 mm. It is preferred if it lies in a range extending from approximately 0.4 mm up to approximately 0.9 mm. It is further preferred if it lies in a range from approximately 0.5 mm up to approximately 0.7 mm. For example, the thickness 78 can have a value of approximately 0.775 mm. In the exemplary embodiments illustrated in the Figures, an internal radius of the curved sections 46, 50 amounts to approximately 1.6 mm, an external radius to approximately 2.2 mm. Both radii can vary accordingly in dependence on the thickness 76.

For the purposes of increasing the fatigue strength of the connecting element 18, the outer surface 80 thereof can be worked at least partially by means of a blasting process.

Furthermore, the connecting element 18 comprises a stiffness-modifying element 80. As illustrated in FIGS. 3a to 8b, this can be formed in different ways and be manufactured in the manner described below.

In FIG. 3a, there is schematically illustrated an arrangement depicting how two indentations 86 and 88 separated by a partitioning element 84 are initially formed by means of two rotating face or milling cutters 82 for the purposes of forming the recess 68. Due to manufacturing tolerances, the leaf spring surface sections 90 and 92 bounding the indentations 86 and 88 do not lie on the same line, i.e. they define different respective planars 94 and 96. Were the face or milling cutter 82 forming the indentation 86 to be displaced further in the direction of the indentation 88 whereby the partitioning element 84 would then be removed completely, a single-step misalignment between the planars 94 and 96, which are defined by the leaf spring surface sections 90 and 92, would develop in the transition region.

In principle, it would be possible to leave in place the partitioning element 84 which is in the form of a wall in the manner of a "webbing". However, as illustrated in FIG. 3a, the partitioning element 84 can be almost completely removed by means of one of the face or milling cutters 82, whereby it does not matter from which of the indentations 86 or 88 this starts.

Initially leaving the partitioning element 84 in its entirety during the production of the connecting element 18 has the especial advantage that manufacturing tolerances are further reducible in contrast to a direct through-milling process since the basic stiffness of the connecting element is significantly increased in the production process. Thus, when milling the connecting element 18 from a solid material, distortions can no longer occur in practice, or at least this danger will then be significantly reduced.

If, in the described manner, the partitioning element 84 is not completely removed, there remains a very small projection in the form of a stiffening projection 98 which defines the stiffness-modifying element 80. An end face 102 of the stiffening projection 98 protruding from the surface 100 of the leaf spring element defines a third planar 104 so that in all, two step-like shoulders 106 and 108 are formed, namely, between the planar 94 and the planar 102 on the one hand and between the planar 102 and the planar 96 on the other.

In the end, a width 110 and also a height 112 of the stiffening projection 98 taken with reference to one of the two planars 94 or 96 determine the change in stiffness of the intermediate section 24 compared with the stiffness thereof without a stiffness-modifying element 80.

As an alternative to the stiffening projection 98, a stiffening groove 114 could also be formed by means of a T-type milling tool 116 as is illustrated schematically in FIG. 3b. For the same thickness of the leaf spring element 25, a very small reduction in the stiffness of the leaf spring element 25 can be achieved in this way. Before forming the stiffening groove 114, the preferably initially produced partitioning element 84 is completely removed, namely, from one side, for example, commencing from the indentation 86, the partitioning element 84 is completely milled out by means of the face or milling cutter 83. This thus results in a direct misalignment between the planars 94 and 96. If the stiffening groove 114 is created in the vicinity of the misalignment that was produced in this way, then a third planar 118 is defined. Basically, the width 120 of the stiffening groove 114 is defined by the thickness or the width of the T-type milling tool 116.

The wall thickness of the partitioning element 84 preferably ranges from approximately 0.3 mm to approximately 0.5 mm. In consequence, this makes it sufficiently stable to prevent deformation of the intermediate section 24 when the latter is being formed from a solid material by means of a material-removing process. On the other hand, such a partitioning element 84 can be totally or partially cut-out using very small cutting forces.

In the manner described, the leaf spring section 25 can be equipped with a stiffness-modifying element 80 both on the surface 100 of the leaf spring element and on a surface 101 of the leaf spring element facing in the opposite direction. It is however also conceivable to equip just one of the two surfaces 100 or 101 of the leaf spring element with a stiffness-modifying element 80. Self evidently, a plurality of stiffness-modifying elements 80 could also be provided and these may optionally be in the form of a stiffening projection or a stiffening groove.

A further exemplary embodiment of a connecting element 18 is illustrated in FIGS. 4a and 4b. It differs from the connecting element 18 illustrated in FIG. 2 by the configuration of the stiffness-modifying element 80. This basically takes the form of a continuous partition wall 122 which encloses the leaf spring element 25 practically completely. In the side view of the connecting element 18 illustrated in FIG. 4b, it is apparent that in a plan or a side view of the connecting element 18 the outer contour 124 of the partition wall 122 is in the form of a rectangle with rounded off corners. The outer contour 124 juts out somewhat from the leaf spring element 25 in a direction transverse to the longitudinal axis 40.

The exemplary embodiment illustrated in FIGS. 4a and 4b can also be regarded, in particular, as an intermediate stage in the production of the exemplary embodiment illustrated in FIG. 2. Stiffening projections 98 or stiffening grooves 114 can be selectively formed on the respective surfaces 100 or 101 of the leaf spring element by complete or partial removal of the partition wall 122.

The exemplary embodiment of a connecting element 18 illustrated in FIGS. 5a and 5b differs from the connecting element 18 illustrated in FIGS. 4a and 4b in that through holes 126 and 128, which are enclosed on all sides, are provided in the vicinity of the respective recesses 66 and 68. The through holes 126 and 128 are each bounded in part by the remaining partition wall 122 and partly by the leaf spring element 25. Overall, the outer contour 124 of the partition wall 122 thus remains virtually the same. Two outer web elements 130 and 132 running parallel to the longitudinal axis 40 thereby remain, these elements serving to interconnect respective neighbouring curved sections 46 and neighbouring curved sections 50 in pairs and so they somewhat stiffen the intermediate section 24.

In the further exemplary embodiment of a connecting element 18 illustrated in FIGS. 6a and 6b, the stiffness-modifying element 80 is likewise in the form of a partially removed partition wall 122. This can be achieved for example in that the contour 134 of the partitioning element 84 in the case of a connecting element 18 of the type disclosed in the exemplary embodiment illustrated in FIGS. 4a and 4b is selected in such a way that it closes off the sides flush with the curved sections 46 and 50. Again, web elements 130 and 132 are thereby formed which interconnect and stiffen the neighbouring curved sections 46 and 50 in pairs. Moreover, the partition wall 122 in the connecting element 18 illustrated in FIGS. 6a and 6b is likewise provided with through holes 126 and 128 in the vicinity of the respective recesses 66 and 68.

In the exemplary embodiment of a connecting element 18 illustrated in FIGS. 7a and 7b, partition walls 136 and 138 remain only in the vicinity of the recesses 66 and 68, but these however, are not in contact with one another. They each extend between mutually opposite and mutually facing surface sections of one of the two surfaces 100 and 101 of the leaf spring element. The partition walls 136 and 138 do not extend quite as far as the entrance openings 70 and 72, but they directly adjoin the inner surfaces of the curved sections 46 and 50 which bound the recesses 66 and 68.

The exemplary embodiment illustrated in FIGS. 8a and 8b differs from the connecting element 18 such as is illustrated in FIGS. 7a and 7b, in that it comprises circular through holes in the partition walls 136 and 138 directly adjacent to the curved sections 46 and 50 in the region of the recesses 66 and 68 as can be perceived from the side view depicted in FIG. 8b. This thus results in web-like partition wall sections which interconnect mutually opposite planar sections 48 and 54 and thereby somewhat increase the stiffness of the leaf spring element 25 in this way.

The exemplary embodiments of connecting elements 18 that are illustrated in FIGS. 4a to 8b, may, as described in connection with FIGS. 3a and 3b, merely form preliminary stages of the process for forming the stiffening projections and stiffening grooves which, for example, are only formed in the region in which the connecting elements 18 comprise partitioning elements 84 such as those described and illustrated in FIGS. 4a to 8b.

The partitioning elements 84 which are formed like webbing can also be used for the fine adjustment of the spring stiffness in the direction of the longitudinal axis 40. The actually achieved nominal dimensions within the tolerance range can be measured during the production process. In a next step, the necessary size or the excess amount for the then still remaining partitioning element 84 is determined and milled accordingly. In particular, the width 110 and also the height 112 of a stiffening projection 98 can thus be determined, and, in analogous manner, the dimensions of a stiffening groove and possibly also the size of the through holes 126 and 128 or 140 and 142 can also be determined. This is possible due to the fact that the geometrical influence of the remaining partitioning element 84 in the form of the stiffening projection 98 for example is substantially smaller than the thickness of the leaf spring itself.

FIG. 9 shows a diagram in which there is illustrated the effect of the thickness of the leaf spring element 25 without a stiffening projection 98 (drawn in broken lines) and the effect of the total thickness of the leaf spring element 25 with a stiffening projection 98 (drawn in a solid line) upon an increase in stiffness. In the given example, one can see that the axial stiffness increases by 20% for a change of thickness 76 or 78 from e.g. 0.75 mm to 0.8 mm in the case where a stiffening projection is not provided. In contrast thereto, one only achieves the same increase in stiffness with a substantially larger increase of the stiffening projection 98, here for example, about 0.3 mm per side.

The diagram in FIG. 9 thus clearly shows that changes of stiffness, which are caused by the tolerances in the thickness 76 or 78, react very sensitively. Nevertheless, they can be compensated by the far less sensitive tolerances in the height of the stiffening projection 98 or possibly the depth of a corresponding stiffening groove.

As already described above, it is also possible to leave the partitioning element 84 in place, as is illustrated in FIGS. 4a and 4b for example. This enables an operating surgeon to remove a part of the partitioning element 84 intra-operatively as required. This gives rise to the possibility of setting the stiffness of the connecting element 18 on an individual basis. The removal process can, for example, be effected with a punch having a jaw geometry corresponding to the leaf spring element 25.

The leaf spring elements 25 described above preferably comprise two shoulders, this arrangement providing greater stability for the leaf spring element 25 during the manufacturing process. Manufacturing tolerances in particular can be compensated for in this way and the surface quality of the intermediate section 24 is improved. As has been mentioned, a stiffening projection 98 or a stiffening groove 114 can be used for the fine adjustment of the axial stiffness, both in the manufacturing process and intra-operatively.

The connecting elements 18 described may be made from metallic materials or synthetic materials, for example, from the materials that have already been mentioned above.

What is claimed is:

1. A connecting element for a spinal column stabilization system comprising a first attachment section for fixing to a first bone attachment device, a second attachment section for fixing to a second bone attachment device and an at least partially flexible intermediate section which is arranged or formed between the first and the second attachment section, which said intermediate section is in the form of a strip-like, winding leaf spring element comprising two leaf spring element surfaces and comprises at least one recess which is open in a direction transverse to a longitudinal axis defined by the intermediate section, wherein at least one of the two leaf spring element surfaces of the leaf spring element comprises at least one stiffness-modifying element, wherein the at least one recess is formed by milling from both sides of the intermediate section in mutually facing directions that are transverse to a longitudinal axis defined by the connecting element and an overall milling depth being smaller in a direction transverse to the longitudinal axis than a thickness of the connecting element in a milling direction transverse to the longitudinal axis, so that a partitioning element separating two milled-out indentations from each other is formed which comprises the at least one stiffness-modifying element.

2. A connecting element in accordance with claim 1, wherein the at least one stiffness-modifying element and the leaf spring element are formed in one piece manner.

3. A connecting element in accordance with claim 1, wherein the at least one stiffness-modifying element is formed in strip-like manner.

4. A connecting element in accordance with claim 1, wherein both leaf spring element surfaces of the leaf spring element each comprise at least one stiffness-modifying element.

5. A connecting element in accordance with claim 1, wherein the at least one stiffness-modifying element is in the form of a stiffening projection which protrudes from one of the two surfaces of the leaf spring element.

6. A connecting element in accordance with claim 1, wherein the at least one stiffness-modifying element extends between two mutually facing surface sections of one of the two surfaces of the leaf spring element.

7. A connecting element in accordance with claim 1, wherein the at least one stiffness-modifying element is arranged in the region of the at least one recess.

8. A connecting element in accordance with claim 1, wherein the connecting element is formed mirror-symmetrically or substantially mirror-symmetrically with respect to a mirror plane.

9. A connecting element in accordance with claim 8, wherein the at least one stiffness-modifying element is formed mirror-symmetrically or substantially mirror-symmetrically with respect to the mirror plane.

10. A connecting element in accordance with claim 1, wherein the leaf spring element is of a different thickness on one side and on another side of the at least one stiffness-modifying element.

11. A connecting element in accordance with claim 1, further comprising at least one through opening which extends transversely of a longitudinal axis defined by the connecting element and is bounded at least in sections by the at least one stiffness-modifying element.

12. A connecting element in accordance with claim 1, wherein a thickness of the at least one stiffness-modifying element in a direction transverse or substantially transverse to a longitudinal axis defined by the connecting element corresponds maximally to approximately a thickness of the leaf spring element and wherein the thickness of the at least one stiffness-modifying element lies in a range extending from approximately 0.2 mm up to approximately 0.6 mm.

13. A connecting element in accordance with claim 12, wherein the thickness of the at least one stiffness-modifying element lies in a range extending from approximately 0.3 mm up to approximately 0.5 mm.

14. A connecting element in accordance with claim 1, wherein a thickness of the leaf spring element lies in a range from approximately 0.5 mm up to approximately 1.5 mm.

15. A connecting element in accordance with claim 1, wherein at least one of the two leaf spring element surfaces comprises at least two step-like shoulders so that the at least one of the two leaf spring element surfaces of the leaf spring element comprises at least two mutually parallel leaf spring surface sections.

16. A connecting element in accordance with claim 1, wherein the connecting element is made from a solid material by a material-removing machining process.

17. A connecting element in accordance with claim 1, wherein the connecting element is made of a metallic material or of a synthetic material.

18. A spinal column stabilization system comprising at least one first bone attachment device, at least one second bone attachment device and a connecting element, which connecting element comprises a first attachment section for fixing to the at least one first bone attachment device, a second bone attachment section for fixing to the at least one second bone attachment device and an at least partially flexible intermediate section that is arranged or formed between the first and the second attachment section, wherein the intermediate section is in the form of a strip-like, winding leaf spring element comprising two leaf spring element surfaces and comprises at least one recess which is open in a direction transverse to a longitudinal axis defined by the intermediate section, wherein at least one of the two leaf spring element surfaces of the leaf spring element comprises at least one stiffness-modifying element, wherein the at least one recess is formed by milling from both sides of the intermediate section in mutually facing directions that are transverse to a longitudinal axis defined by the connecting element and an overall milling depth being smaller in a direction transverse to the longitudinal axis than a thickness of the connecting element in a milling direction transverse to the longitudinal axis, so that a partitioning element separating two milled-out indentations from each other is formed which comprises the at least one stiffness-modifying element.

19. A spinal column stabilization system in accordance with claim 18, wherein at least one of the two leaf spring element surfaces comprises at least two step-like shoulders so that the at least one of the two surfaces of the leaf spring element comprises at least two, preferably three flat, mutually parallel leaf spring surface sections.

20. A method of manufacturing a connecting element for a spinal column stabilization system comprising the steps of:
   forming a first attachment section for fixing to a first bone attachment device,
   forming a second bone attachment section for fixing to a second bone attachment device and forming or arranging an at least partially flexible intermediate section between the first and the second attachment section, wherein the intermediate section is formed as a strip-like, winding leaf spring element comprising two leaf spring element surfaces and comprises at least one recess which is open in a direction transverse to a longitudinal axis defined by the intermediate section,
   forming at least one stiffness-modifying element on at least one of the two leaf spring element surfaces of the leaf spring element, and
   forming the at least one recess by milling from both sides of the intermediate section in mutually facing directions that are transverse to a longitudinal axis defined by the connecting element and with an overall milling depth being smaller in a direction transverse to the longitudinal axis than a thickness of the connecting element in a milling direction transverse to the longitudinal axis, so that a partitioning element separating two milled-out indentations from each other is formed.

21. A method in accordance with claim 20, wherein the leaf spring element is made from a solid material by a material-removing machining process.

22. A method in accordance with claim 21, wherein the material-removing process is effected by a milling process.

23. A method in accordance with claim 20, wherein at least one of the first and the second attachment section are made from a solid material by a material-removing machining process.

24. A method in accordance with claim 20, characterized in that the partitioning element is in the form of a wall.

25. A method in accordance with claim 20, wherein the partitioning element is partly removed.

* * * * *